United States Patent [19]
Lin et al.

[11] Patent Number: 5,861,319
[45] Date of Patent: Jan. 19, 1999

[54] IMMOBILIZATION OF SPECIFIC BINDING ASSAY REAGENTS

[75] Inventors: Spencer H. Lin, Coral Springs; Kwok Sum Yu, Winter Springs; Pratap Singh, Miami; Steven E. Diamond, Coral Springs, all of Fla.

[73] Assignee: Dade Behring Inc., Deerfield, Ill.

[21] Appl. No.: 331,243

[22] Filed: Oct. 28, 1994

Related U.S. Application Data

[63] Continuation of Ser. No. 21,928, Feb. 24, 1993.

[51] Int. Cl.$^6$ .......................... G01N 33/552; G01N 33/78
[52] U.S. Cl. .......................... 436/527; 435/7.93; 435/7.94; 435/817; 435/823; 436/500; 436/505; 436/512; 436/530; 530/391.1; 530/811
[58] Field of Search .................... 436/500, 512, 436/527, 530, 823; 435/7.93, 7.94

[56] References Cited

U.S. PATENT DOCUMENTS

| | | | |
|---|---|---|---|
| 4,363,634 | 12/1982 | Schall, Jr. | 23/230 B |
| 4,507,466 | 3/1985 | Tomalia et al. | 528/332 |
| 4,517,288 | 5/1985 | Giegel et al. | 435/188 |
| 4,568,737 | 2/1986 | Tomalia et al. | 528/332 |
| 4,694,064 | 9/1987 | Tomalia et al. | 528/332 |
| 5,204,448 | 4/1993 | Subramanian | 530/391.5 |
| 5,338,532 | 8/1994 | Tomalia et al. | 424/1.49 |
| 5,418,136 | 5/1995 | Miller et al. | 436/527 |
| 5,468,606 | 11/1995 | Bogart et al. | 436/531 |
| 5,482,830 | 1/1996 | Bogart et al. | 436/513 |
| 5,541,057 | 7/1996 | Bogart et al. | 436/531 |

FOREIGN PATENT DOCUMENTS

| | | |
|---|---|---|
| 0481526 | 4/1992 | European Pat. Off. . |
| WO 8801178 | 2/1988 | WIPO . |
| 9012050 | 10/1990 | WIPO . |
| 9112886 | 9/1991 | WIPO . |
| WO 91/12886 | 9/1991 | WIPO . |
| 9306868 | 4/1993 | WIPO . |
| WO 94/03774 | 2/1994 | WIPO . |

OTHER PUBLICATIONS

Giegel et al., *Clin. Chem.* 28: 1894–98 (1982).
Roberts, J.C. et al., Using Starburst Dendrimers as Linker Molecules to Radiolabel Antibodies, *Bioconjug. Chemistry* 1: 305–308 (1990).

*Primary Examiner*—Mary E. Ceperley
*Attorney, Agent, or Firm*—Ronald C Lundquist

[57] ABSTRACT

Methods and compositions are provided for specific binding assays in which specific binding reagents are immobilized on a solid phase. Immobilization is facilitated by covalently coupling specific binding assay reagents such as polypeptide receptors or analytes with water soluble polymers. Such water soluble polymers, for example star polymers such as dendrimers, provide production advantages of lot-to-lot uniformity and homogeneity, and can enhance sensitivity due to low non-specific binding to the solid phase.

36 Claims, 5 Drawing Sheets

IMMOBILIZATION OF SPECIFIC BINDING ASSAY REAGENTS

This is a continuation of U.S. Ser. No. 08/021,928 filed Feb. 24, 1993.

FIELD OF THE INVENTION

This invention relates generally to the field of methods for immobilizing specific binding assay reagents on a solid support. In particular this invention relates to a method to immobilize reagents onto a solid phase support using water soluble polymers. This invention also relates to a solid phase support having immobilized reagents useful in diagnostics tests.

BACKGROUND OF THE INVENTION

In vitro diagnostic assays may be used to measure amounts of an analyte found in a body fluid sample or tissue sample. The analyte must be distinguished from other components found in the sample. Analytes may be distinguished from other sample components by reacting the analyte with a specific receptor for that analyte. Assays that utilize specific receptors to distinguish and quantify analytes are often called specific binding assays.

The most common receptors are antibodies and specific binding proteins such as Intrinsic Factor or Folate Binding Protein. Receptors are characterized by having a reversible specific binding affinity for an analyte or an analogue of that analyte. The analogue generally is an analyte derivative carrying a detectable marker such as an enzyme, fluorescent molecule or other known label but which binds to a receptor with about the same specificity and affinity as the analyte.

In heterogeneous specific binding assays described in the technical and patent literature, the receptor or other assay reagent of the specific binding reaction is often immobilized on a solid phase. Immobilization of these reagents is required to separate the bound components (for example analyte bound to the solid phase through a receptor) from the unbound components.

The various methods by which a receptor or other reagent can be immobilized on a solid phase include adsorption, absorption or covalent bonding. However, many of the solid phase supports used in such assays are not inert, and may sequester proteins and other substances from the sample by non-specific binding. Although glass is a relatively inert substrate, generally it has been found to be unsatisfactory for use in solid phase binding assays. See, for example U.S. Pat. No. 3,790,653 for a discussion of inadequacies of glass substrates.

Recently, however, procedures have been described for immobilizing an essentially soluble immunocomplex of a reagent and an antiserum to the reagent on an inert glass fiber solid phase support. These procedures are disclosed in U.S. Pat. No. 4,517,288, incorporated by reference herein.

In these immunological immobilization procedures, soluble immunocomplexes are prepared by combining at least two immunochemically reactive substances with one another in solution. At least one of such immunochemically reactive materials is selected for its immunochemical specificity for an analyte of interest. For example, if the soluble immunocomplex is to be used in an immunoassay for the detection of TSH, then one component of the immunocomplex is selected for its immunochemical specificity for TSH. A typical example would be an antibody with specificity for TSH, i.e., an anti-TSH antibody. The second component of the immunocomplex could comprise an antibody preparation directed against the anti-TSH antibody. Antiserum to anti-analyte antibodies, for example to mouse anti-TSH antibodies, can be prepared by injecting purified mouse IgG into a host animal (i.e., goat), and thereafter harvesting the antiserum to the mouse IgG. The mouse anti-TSH antibody and the goat antiserum to mouse IgG are thereafter worked up as standard stock solutions.

Once having prepared these stock solutions, a portion of each is combined with the other by addition to a buffered medium. The resulting immunocomplex, in an appropriate volume of buffer, is thereafter spotted onto a delimited area of a glass fiber filter. Alternatively, the two components of the immunocomplex may be applied to the filter as separate buffered solutions and allowed to react in situ. In both instances, the point of application of the immunocomplex defines a reaction zone within the solid phase. The applied immunocomplexes become adsorbed and entrapped within the interstices of the beds of fibers within the glass fiber filter. The method of application can include dispensing of the immunocomplex solution with a manual or automated pipette, or with other automated equipment including assay analyzer instruments. Subsequent to application of the immunocomplex to the solid phase and the elapse of a suitable incubation period, the solid phase is dried under controlled conditions thereby yielding a stable reactive reagent which can be used in any one of a number of solid phase specific binding assay protocols.

Immunological immobilization, although useful in a variety of assay formats, has been noted to include a number of inherent disadvantages. The presence of the additional immunoglobulins on the filter (e.g., antiserum to anti-analyte antibodies) can lead to nonspecific binding of proteinaceous and other biological materials. This can significantly decrease assay sensitivity. Moreover, given the inherent variability of IgG preparations from separate immunizations of the same or different host animals, lot-to-lot variability in titer, purity, specificity and affinity of IgG preparations must be accounted for in manufacturing procedures. Similarly, variability in production of solid phase reagents may be encountered due to the tendency of immunocomplexes to become inhomogeneously distributed within stock solutions. That is, such immunocomplexes, while substantially soluble, may not remain completely soluble and may undergo some settling out of solution over time. Even with periodic mixing of stock solutions, gravitational influences, temperature gradients and other physical influences can cause subtle inhomogeneities within solutions applied to the solid phase reagents.

Starburst dendrimers (manufactured by The Dow Chemical Company) are polymers of spherical or other three-dimensional shapes that have precisely defined compositions and that possess a precisely defined molecular weight. Such dendrimers can be synthesized as water soluble macromolecules through appropriate selection of internal and external moieties. See U.S. Pat. Nos. 4,507,466 and 4,568,737, incorporated by reference herein. Dendrimers may be conjugated with various pharmaceutical materials as well as with various targeting molecules that may function to direct the conjugates to selected body locations for diagnostic or therapeutic applications. See for example, WO 8801178, incorporated by reference herein. Starburst dendrimers have been used to covalently couple synthetic porphyrins (e.g., hemes, chlorophyll) to antibody molecules as a means for increasing the specific activity of radiolabeled antibodies for tumor therapy and diagnosis. Roberts, J. C. et al., Using Starburst dendrimers as Linker Molecules to Radiolabel Antibodies, *Bioconjug. Chemistry* 1: 305–308 (1990).

SUMMARY OF THE INVENTION

The present invention relates to a method of preparing a solid phase support by covalently coupling a specific binding assay reagent to a dendrimer and immobilizing the dendrimer-reagent complex within a delimited area of a solid phase support. A reagent such as a receptor is covalently coupled to a dendrimer by coupling methods which include but are not limited to the formation of carbon-nitrogen (C—N) linkages. Such C—N linkages may be formed, for example, by oxidizing the carbohydrate moiety of the receptor to form aldehydes, combining the receptor with the dendrimer, then reducing the resulting Schiff's bases. Other methods for coupling the receptor to the dendrimer include but are not limited to the formation of carbon-sulfur (C—S) and carbon-oxygen (C—O) linkages. The C—S linkages may be formed, for example, by combining sulfosuccinimidyl-(4-iodoacetyl) aminobenzoate (SIAB)-labeled dendrimers with sulfhydryl-containing receptors. The C—O linkages may be formed, for example by reaction of amino groups of the receptors with cyanogen bromide-activated dendrimers.

The reagents can be, without limitation, antibodies or antibody fragments, binding proteins, other polypeptides or various bio-active non-proteinaceous molecules. The dendrimers useful in the present invention include without limitation water soluble dendrimers having reactive functional terminal groups. Such reactive functional terminal groups include without limitation amino, carboxyl and sulfhydryl functional groups. The dendrimers can have various fixed diameters including without limitation 22 Angstroms (Å), 54 Å, 95 Å, and larger fixed diameters. The preferred fixed diameters are 54 Å and 95 Å, and the most preferred fixed diameter is 54 Å.

The present invention also includes a specific binding assay complex comprising a solid phase having adsorbed thereto a dendrimer-reagent complex. The preferred solid phase is a porous inert solid phase. The dendrimer-reagent complex is prepared by covalently attaching the reagent to the dendrimer.

The present invention also comprises a method for conducting a solid phase binding assay using a dendrimer-reagent complex to determine the concentration or presence of an analyte in a sample.

DETAILED DESCRIPTION

The dendrimers most useful in preparing the solid phase supports of the present invention are generally spherical branched polymers having "star" configurations as disclosed in U.S. Pat. No. 4,507,466. The star configuration derives from a structured branching wherein individual branches radiate out from a nucleus, or core region. The polyvalent core is covalently bonded to at least two ordered dendritic (tree-like) branches which extend through at least two tiers, or generations. The outermost tier or generation may be derivatized to terminate in functional groups that may be chemically reactive with a variety of other molecules. Thus, star dendrimers are unitary molecular assemblages that possess three distinguishing architectural features, namely (a) an initiator core, (b) interior layers (generations) composed of repeating units radially attached to the initiator core, and (c) an exterior surface of terminal functionality attached to the outermost generation.

The size, shape and reactivity of a dendrimer can be controlled by the choice of the initiator core, the number of generations employed in creating the dendrimer, and the choice of the repeating units employed at each generation. Depending on the number of generations employed, dendrimers of discrete sizes are readily obtained. In addition, chemical modification of all or a portion of the surface moieties may create new surface functionalities appropriate for particular diagnostic or therapeutic operations. Generally spherical dendrimers of configurations suitable for use in the present invention are disclosed in U.S. Pat. No. 4,507,466 and U.S. Pat. No. 4,568,737. Alternatively, dendrimers of non-spherical configuration, such as those disclosed in U.S. Pat. No. 4,694,064, may be adapted for use in the present invention. Preferably, the dendrimers have an outer functionalized surface having amine-terminated functional groups.

Figure 1:
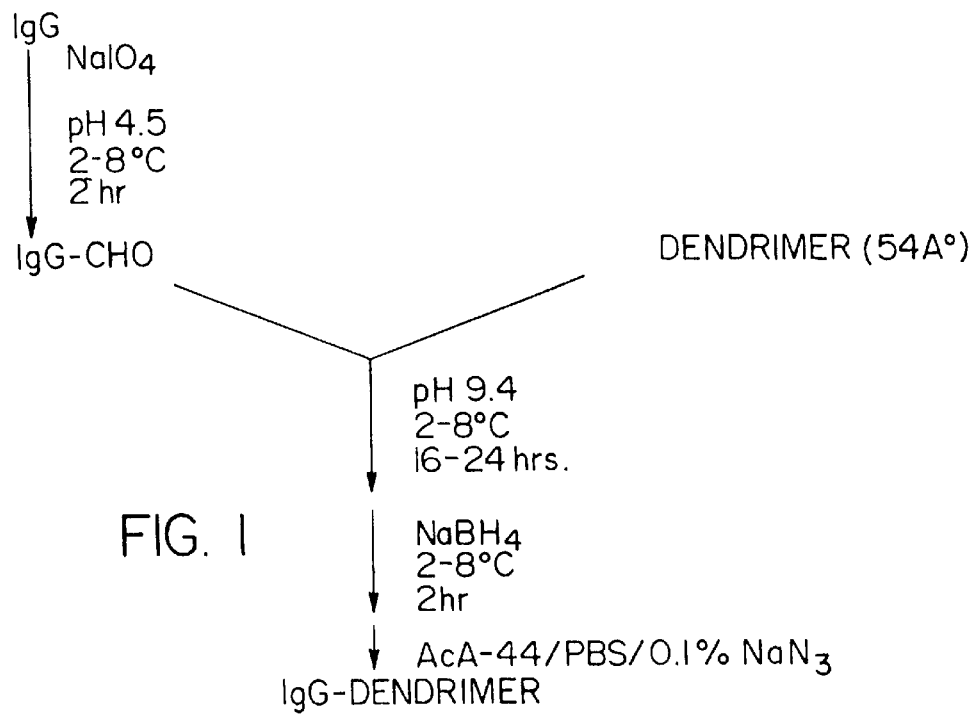
FIG. 1 is a schematic representation of the Schiff base chemistry for production of C—N linkages in dendrimer-reagent complexes, using as an example an antibody (IgG) reagent.

A variety of reliable and reproducible chemistries are available for attachment of specific binding assay reagents to the outer functionalized surfaces of dendrimers. For example, periodate-oxidized antibody may be coupled to the dendrimers, followed by borohydride reduction of the resulting Schiff's bases. This method for formation of C—N linkages is depicted schematically in FIG. 1. Preferably, 54 Å dendrimers are used for coupling with appropriate assay agents. This dendrimer is a fifth-generation particle having 96 amine-terminated end (surface) groups and a molecular weight of 21,590. The amine-terminated end groups impart a net positive charge to the surfaces of such dendrimers under normal assay conditions.

Figure 2:
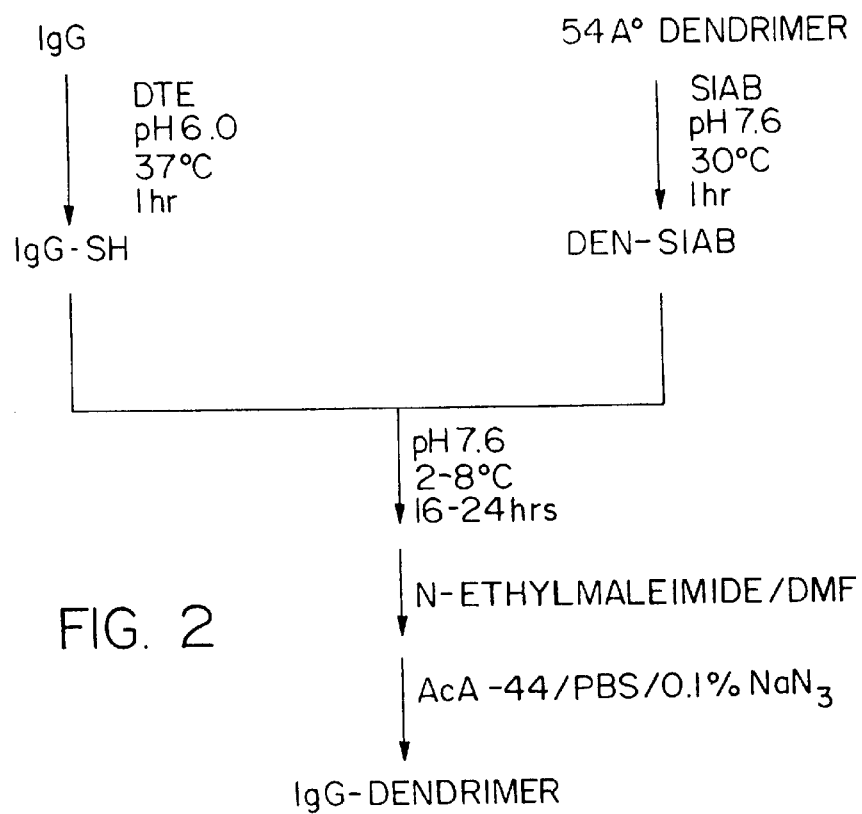
FIG. 2 is a schematic representation of the sulfosuccinimidyl-(4-iodoacetyl) aminobenzoate (SIAB)-based chemistry for production of C—S linkages in dendrimer-reagent complexes, using as an example an antibody (IgG) reagent.

Alternatively, specific binding assay reagents may be attached to the dendrimers by formation of C—S linkages by combining dendrimers derivatized with SIAB with sulfhydryl-containing assay reagents. Preparation of dendrimer-reagent complexes through use of SIAB chemistry is depicted schematically in FIG. 2.

Dendrimer surface functional groups in addition to amino terminal groups include hydroxy, mercapto, carboxyl, alkenyl, allyl, vinyl, amido, halo, urea, oxiranyl, aziridinyl, oxazolinyl, imidazolinyl, sulfonato, phosphonato, isocyanato and isothiocyanato. Various known chemistries are usable with this wide range of surface functional groups and are useful for attachment of assay reagents to such functional groups.

Applicants have discovered that dendrimer-reagent complexes may be used for immobilization of reagents on a specific binding assay solid phase. While such complexes are useful for preparation of various solid phase reagents in immuno and other assays, the applicants have found a particularly useful application of such complexes in use with glass fiber filter substrates and radial partition assays. Radial partition immunoassay as disclosed in Giegel et al., Clin. Chem. 28:1894–98 (1982) and in U.S. Pat. No. 4,517,288 is an assay procedure in which all steps are conducted directly on a solid phase. Antibody or other reagent is immobilized on a small area of glass fiber filter paper. Various calibrators containing known amounts of an analyte to be detected or various unknown samples potentially containing such analyte are then allowed to react with this immobilized receptor. Following appropriate additions of labeled analogues or other labeling reagents, excess reagents are removed from the center area of filter paper by application of a wash fluid. In the case of an enzyme immunoassay, the wash fluid may contain the substrate for the enzyme, thus initiating the enzyme reaction simultaneously with the wash step. Preferably the action of the enzyme on the substrate generates a fluorescent signal. The enzyme activity in a part of the center area is then quantifiable by front-surface fluorometry. Depending on the assay format, i.e., direct binding assay or competitive assay, the rate of fluorescence is directly or inversely proportional to the concentration of analyte in the sample.

As described above, it is preferred that the solid phase present a relatively "inert" surface. That is, the surface should be relatively nonreactive with biological materials, particularly with respect to nondiscriminate adsorption of proteinaceous materials. In the preferred embodiments of this invention, the physical form of the solid phase is such that the interstices or pores within the solid phase are sufficiently small so that the reaction fluids are retained and transported by capillary action. On the other hand, the solid phase pores or interstices should not be so small so as to retain undesirable components that might give rise to false positive signals.

The solid phase is advantageously composed of a mat of compressed fibers, such as glass or synthetic fibers or relatively inert cellulosic materials. The solid phase also may be constructed of other porous constituents such as sintered glass, ceramics and synthetic polymeric materials. Glass fiber filter paper is the preferred solid support of the present invention because of its inert characteristic and because of its ability to adsorb the soluble complexes of this invention in quantities sufficient for quantitative evaluation of retention of assay reagents. The surfaces of the glass fibers may carry a net negative charge, which facilitates adsorption of dendrimers having substantially positively charged surfaces under assay conditions, i.e., dendrimers with amine terminal surface groups.

The dendrimer-reagent complexes of this invention, once adsorbed onto a suitable solid phase, can be used in a wide variety of analytical protocols for analysis of a variety of biological materials. For example, dendrimer-receptor complexes may be useful for immunoassay of blood or urine for the presence of therapeutic drugs, natural or synthetic steroids, hormones, enzymes, antibodies and other analytes of interest.

Therapeutic agents that can be analyzed in such protocols include without limitation digoxin, dilantin, phenobarbital, theophylline, gentamicin, quinidine, and the like. Solid phases prepared in the foregoing manner can also be used in immunoassays for the detection of steroids such as cortisol, aldosterone, testosterone, progesterone, and estriol or serum protein such as ferritin. Hormone levels are also capable of determination through the use of solid phase complexes of the present invention. These hormones include without limitation thyroid hormones such as tetraiodo- and triiodothyronine and thyroid stimulating hormone (TSH); peptide hormones such as insulin, corticotropin, gastrin, angiotensin, and proangiotensin; and polypeptide hormones such as thyrotropin, levteotropin, somatotropin and human chorionic gonadotropic hormone (HCG). Other applications of the complexes of the present invention include assay of relatively small molecules involved in metabolism, i.e., folate, to assay of polypeptide antigens and antibodies associated with infectious disease, i.e., antigens and antibodies associated with HIV, hepatitis, CMV, syphilis, Lyme disease agents, and numerous other infectious agents.

Applicants have discovered that dendrimers can be used in place of antiserum to facilitate immobilization of assay reagents on the solid phase. That is, dendrimers can be covalently coupled to assay reagents such as antibodies or even relatively small molecules, and then immobilized on glass fiber filters. In comparison to immunological immobilization, immobilization utilizing dendrimer complexes presents a number of distinct advantages. First, the dendrimers are produced with precise polymer chemistries and can be designed to have a precise number of generations yielding a precise molecular size, weight and surface composition. Because of the uniform and characterized chemistries, such parameters remain uniform over different manufacturing lots. Second, the dendrimers, depending on interior and surface compositions, can be manufactured to be water soluble such that the dendrimer-reagent conjugates remain in solution and maintain solution homogeneity over time. This eliminates lot-to-lot nonuniformity due to inhomogeneous distribution of immunological conjugates in solution. Third, the chemistries for attachment of reagents to the dendrimers are well characterized and are not subject to the variations inherent in associations of antisera and antibody binding substances. Antisera are subject to variations in affinity, specificity, and immunoglobulin purity, none of which are encountered during production of dendrimer-reagent conjugates.

For these reasons, dendrimer-based solid phase reagents are readily prepared having substantial lot-to-lot uniformity. Moreover, since stock or commercial solutions of dendrimer conjugates retain homogeneity over substantial periods of time, it is possible for end users of commercial assay instruments to prepare these solid phase reagents on site. The use of freshly prepared solid phase reagents further eliminates additional variables that may enter into distribution and commercial use of pre-prepared solid phase reagents, such as changes due to long term storage, temperature of storage, and other storage variables.

Assay reagents such as receptors may be coupled to the dendrimers via Schiff base linkage, SIAB linkage or other methods and then applied to solid phase materials such as glass fiber filters. In a preferred embodiment, "tabs" as marketed by Baxter Diagnostics Inc. are assembled from GF/F glass filter paper distributed by Whatman Inc. and snap-fit plastic tab parts as discussed below. Generally the dendrimer-reagent complexes are applied to the center areas of such tabs in an appropriate buffer solution. Generally such buffers should include surfactants, analyte-free serum albumin and a preservative such as sodium azide. Aliquots of dendrimer complex solution are spotted onto the centers of blank tabs, then oven dried with heat. After cooling, the tabs may be stored under refrigeration.

In an alternative embodiment, the dendrimers themselves may be formed into a solid phase. The dendrimers may be dissolved in appropriate solvents and sprayed or otherwise applied to appropriate solid surfaces. Upon evaporation of the solvent, the dendrimers become concreted into thin films or filaments and can be so isolated. Alternatively, such thin films of concreted dendrimers can be used to coat the internal surfaces of tubes or other containers used in specific binding assays. Assay reagents such as antibodies can be covalently coupled to such dendrimer concretions either before or after application of the sprayed material and subsequent drying period.

The dendrimer-reagent complex/solid phase preparations of the present invention are applicable to a variety of specific binding assay formats. For example, various direct-binding assays may be employed with these reagents. In such assays, receptors such as antibodies or binding proteins are covalently coupled to the dendrimers and immobilized on the solid phase. The immobilized dendrimer-receptor complexes are contacted with a sample containing the analyte of interest. Following binding of the analyte by the immobilized receptor, the solid phase is washed and then contacted with an indicator. The term indicator in the context of this invention means a labeled conjugate. The conjugate comprises an antibody, antibody fragment, binding protein or analyte depending on assay format, and the label is a fluorescent, enzymatic, calorimetric, radiometric or other labeling molecule that is associated either directly or indirectly with the conjugate. The label may be comprised of an enzymatic compound that produces fluorescence upon contact with a substrate. The extent to which the indicator is present on the solid support can be correlated with the amount of unknown analyte as disclosed, for example, in Tijssen, P., *Laboratory Techniques in Biochemistry and Molecular Biology*, Practice and Theory of Enzyme Immunoassay, pp. 173–219 (Chapter 10) and pp. 329–384 (Chapter 14), Elsevier Science Publishers, Amsterdam, The Netherlands, 1985.

The complexes of the present invention also may be used in competitive assay formats. In such formats, the solid phase containing immobilized receptor or other molecule with specificity for a selected analyte is contacted with a sample presumably containing such analyte and with a specific competitive reagent. The specific competitive reagent may be a labeled analogue of the analyte. In this embodiment, the labeled analogue competes with the sample analyte for binding to a receptor immobilized on the solid phase. In an alternative embodiment, analyte may be coupled to a solid phase and contacted with a sample and with a specific competitive reagent, for example a labeled receptor for the analyte. In this format, sample analyte competes with solid phase analyte for binding with soluble labelled receptor. In both embodiments, the amount of label bound to the solid phase after washing provides an indication of the levels of analyte in the sample. That is, the amount of label bound to the soluble phase is inversely proportional to the amount of analyte in the sample.

Various instruments are available for applying the dendrimer-reagent conjugates and various other binding assay reagents to a solid phase, washing, and reading the amounts of indicator bound to the solid phase. In a preferred embodiment, the solid phase comprises the glass fiber filter tabs as described above, and the instrument comprises the Stratus® Immunoassay System, available from Baxter Diagnostics Inc. This instrument is a batch-processing bench-top instrument, described by Giegel et al., Clin. Chem. 28:1894–98 (1982). The instrument is adapted to process tabs in the radial partition immunoassay format, which format is also described in Giegel et al. The instrument includes fluid dispensers for sample, conjugate and substrate washes. Microprocessor-controlled stepping motors aspirate and dispense required aliquots of reagents. All timing and operational aspects of the dispensers are predetermined by a program routine within the analyzer. The instrument also includes a tab transport system, heated platens with temperature monitoring, sample and reagent fluid pumps, a read station, data processing, and means for tab disposal.

For quality control, the instrument microprocessor control program periodically verifies critical operating conditions such as reference voltages, temperatures, and dispensing settings, and flags for out-of-limit values.

The invention will be further understood with reference to the following illustrative embodiments, which are purely exemplary, and should not be taken as limiting the true scope of the present invention as described in the claims.

EXAMPLE 1

Preparation of IgG-Dendrimer via Schiff Base Linkage

An IgG concentrate solution consisting of 4–5 mg IgG/ml in pH 4.5 acetate buffer (0.1M NaOAc/0.1M NaCl) is prepared and chilled on ice. A ⅔ volume of chilled, 0.1M $NaIO_4$ in pH 4.5 acetate buffer is added to the IgG solution and the combined IgG/$NaIO_4$ solution is incubated in the dark for 2 hrs. at 2°–8° C. Ethylene glycol at 10 ul/ml of original IgG concentrate solution is added and the incubation is continued for an additional ½ hr. at 2°–8° C. The resulting solution of IgG-aldehyde derivative (IgG-CHO) is desalted by passage over an appropriately sized column of Sephadex G-25 equilibrated with pH 4.5 acetate buffer. Protein fractions are collected and pooled and the concentration of IgG-CHO is determined spectrophotometrically at 280 nm using an extinction coefficient of 1.48 ml·$mg^{-1}$·$cm^{-1}$. The aldehyde content of the periodate-oxidized IgG may be quantitated using the aldehyde-modifying reagent Purpald (Aldrich, Cat. No. 16-289-2) with appropriate concentrations of formaldehyde as calibrators.

Dendrimers (54 Å particle size) in aqueous solution (Polysciences, Cat. No. 21152) are added to the desalted IgG-CHO solution at a 3:1 molar ratio of dendrimer:IgG-CHO. The combined dendrimer/IgG-CHO is buffer exchanged into 0.1M sodium carbonate buffer, pH 9.4, and the solution volume is adjusted to provide a final IgG concentration of approximately 1.0 mg IgG/ml. The solution is then incubated at 2°–8° C. for 16–24 hrs. Then, a volume of freshly prepared $NaBH_4$ solution (4 mg/ml in water) equal to ¹⁄₂₀ of the volume of the dendrimer/IgG-CHO reaction mixture is slowly added and incubated at 2°–8° C. for an additional 2 hrs. The resulting solution is clarified, if necessary, by filtration through a 0.22 um filter. An appropriately sized column of polyacrylamide-agarose gel matrix (AcA-44 Ultrogel, IBF, Cat. No. 230161) is prepared and equilibrated in phosphate-buffered saline (PBS)/0.1% $NaN_3$. The final dendrimer/IgG-CHO reaction mixture is concentrated to a volume of less than 3% of the AcA-44 bed volume, then loaded onto the column and eluted at an appropriate flow rate. Fractions containing the first protein peak, which comprises the coupled IgG-dendrimer preparation (IgG-DEND), are pooled. The concentration of IgG in the IgG-DEND preparation is determined spectrophotometrically using an extinction coefficient of 1.48 ml·mg$^{-1}$·cm$^{-1}$ at 280 nm.

EXAMPLE 2

Preparation of IgG-Dendrimer via SIAB Linkage

A one-fifth volume of sodium phosphate buffer (0.5M NaH$_2$PO$_4$, pH 7.1) is added to the vendor-supplied aqueous solution of 54 Å dendrimer (Polysciences, Cat. No. 21152). The resulting solution is adjusted to pH 7.6 with 1N HCl or 1N NaOH. An appropriate volume of 15 mg/ml sulfo-SIAB in water is added to the dendrimer solution to equal a 20:1 molar ratio of sulfo-SIAB:dendrimer, then incubated at 30° C. for 1 hr. The resulting solution of SIAB-dendrimer derivative (SIAB-DEND) is loaded onto an appropriately sized column of Sephadex G-25 previously equilibrated with 0.1M NaH$_2$PO$_4$, pH 7.6. Following elution at a flow rate of approximately 0.5 ml/min, the SIAB-DEND fractions are pooled and the concentration of SIAB-DEND is determined with fluorescamine, a fluorogenic reagent used for assay of primary amines, as described in Weigele et al., J. Am. Chem. Soc. 94: 5927 (1972) and in Udenfriend et al., Science 178: 871 (1972). Appropriate concentrations of underivatized 54 Å dendrimer are used as calibrators.

For preparation of sulfhydryl-IgG derivative (IgG-SH), a solution of 5 mg IgG/ml in reduction buffer (0.1M NaH$_2$PO$_4$, 5 mm EDTA, pH 6.0) is prepared. Dithioerythritol (DTE) is dissolved in reduction buffer at a concentration of 11.4 mg/ml. The DTE solution is added to the IgG solution in a volume equal to 1/9 of the volume of the 5 mg/ml solution of IgG, then incubated at 37° C. for 1 hr. The resulting IgG-SH solution is then desalted by passage over an appropriately sized Sephadex G-25 column, and the IgG-SH concentration and SH content determined with standard methods.

Finally, for preparation of IgG-DEND, SIAB-DEND solution is combined with IgG-SH solution at a 3:1 molar ratio of SIAB-DEND: IgG-SH, then buffer-exchanged into sodium phosphate buffer (0.1M NaH$_2$PO$_4$, pH 7.6). The solution is volume-adjusted to a final IgG concentration of approximately 5 mg/ml, then incubated at 2°–8° C. for 16–24 hrs. The reaction is stopped by addition of a 1/50 volume of quenching solution consisting of 10 mg/ml N-ethylmaleimide (NEM) in N,N-dimethylformamide (DMF) followed by an additional incubation at room temperature (23°–25° C.) for 2 hr. The quenched reaction mixture is clarified, if necessary, by passage through a 0.22 um filter, then purified by passage over an AcA-44 Ultrogel column as described in Example 1, above.

EXAMPLE 3

Preparation of Solid Phase Supports (Tabs)

Solid phase supports used in the present experiments comprised "tabs" as used with the Stratus® analyzer instrument or the Stratus® II analyzer instrument, both marketed by Baxter Diagnostics Inc. These tabs are assembled from 1-in. (2.5 cm)-wide rolls of GF/F glass filter paper (Whatman Inc.) and snap-fit plastic tab parts, as disclosed in Giegel et al., Radial Partition Immunoassay, Clin. Chem. 28: 1894–98 (1982). Appropriate concentrations of dendrimer solutions, antibody solutions or other protein or control solutions are made up in spotting buffer. The spotting buffer composition may be varied to accommodate particular experimental or manufacturing parameters. Generally the spotting buffer may comprise, for example, an appropriate buffer including but not limited to 20 mM–200 mM Tris, pH 7.0–9.0, a non-ionic surfactant such as Zonyl® FSN (E. I. DuPont DeNemours & Co., Cat. No. CH 7152S) in a concentration range of 0.1%–1.0%, bovine serum albumin (BSA) at 0.5%–4.0% and 0.1% sodium azide. Preferably the spotting buffer comprises 30–100 mM Tris, pH 7.0–8.5, 0.1%–0.5% Zonyl® FSN, 1.0%–3.0% BSA and 0.1% sodium azide. Most preferably the spotting buffer comprises 50 mM Tris, pH 8.0, 0.1% Zonyl® FSN, 2.0% BSA and 0.1% sodium azide. Fluorinated surfactants (e.g. 3M Cat. No.'s FC 171 and FC 170C) and other appropriate surfactants known to the skilled artisan may be substituted for Zonyl® FSN.

Aliquots of 76 ul of a selected solution are spotted onto the centers of blank tabs, which are then oven-dried at 80°–90° C. After cooling, the tabs may be stored at 2°–8° C. until used. Spotting of the solutions on the tabs may be carried out manually with a pipetting device or may be carried out with automated manufacturing procedures. Alternatively, the tabs may be spotted and processed by the Stratus® II instrument itself, following appropriate programming of machine parameters to apply selected aliquots of stock solutions to the centers of tabs.

EXAMPLE 4

TSH Assay

In preliminary experiments, dendrimers of three different sizes (22 Å, 54 Å and 95 Å) were tested as described below. There was very little difference in performance when particles of 54 Å or 95 Å were used for immobilization, but relatively poorer performance with the 22 Å particles. Although Applicant is not to be held to a particular theory or mechanism, it is possible that a certain minimum size of the immobilized antibody/dendrimer complex is required for optimum adsorption to the surface of the paper. A similar size-related phenomenon has been observed with the current tab formulations using secondary antibodies (rather than dendrimers) for immobilization. Although providing acceptable results under some conditions, use of the larger (95 Å) dendrimer particles normally was accompanied by formation of high molecular weight aggregates. Thus, the 54 Å dendrimers were used for all other experiments reported herein. Dendrimers of other particle sizes, including those of 22 Å, may be appropriate for experimental conditions in which buffer, reagent concentrations and other parameters were varied from those reported herein.

In further experiments, monoclonal antibody CA2-2f (CA2), was coupled to 54 Å dendrimer particles as described above in EXAMPLE 1. CA2 is on deposit at the American Type Culture Collection (ATCC) under Accession Number 1437. This antibody, and a second monoclonal antibody (MAB-2) used in an hTSH assay presently marketed by Baxter Diagnostics Inc., are directed against the beta chain of human thyroid stimulating hormone (hTSH). The antibodies are believed to be directed to similar, if not the same, epitopes, and have similar affinity coefficients in the range of $10^8$ to $10^{10} M^{-1}$. The CA2-dendrimer complexes (CA2-DEND) were spotted onto tabs as described above in EXAMPLE 3 (spotting buffer: 50 mM Tris, pH 8.0, 0.1% Zonyl® FSN, 2.0% BSA and 0.1% sodium azide) and used in a specific binding assay format for hTSH. The amounts of CA-2 DEND spotted on the tabs were in a range of 3.75 ug/tab to 37.5 ug/tab, depending on selected experimental conditions.

A direct specific binding assay was performed in which calibrated amounts of hTSH were spotted on the CA2-DEND tabs, complexed with detector, washed, and the amount of bound hTSH measured by front surface fluorometry in a Stratus® instrument, as described in Giegel et al., Clin. Chem 28: 1894–98 (1982). In these experiments, the detector comprised an enzyme-labeled anti-hTSH antibody conjugate applied as a Tris-buffered solution comprising anti-hTSH monoclonal double antibody (available commercially from Medix, Foster City, Calif., and from Serono Diagnostics, Allentown, Pa.) conjugated with calf intestinal alkaline phosphatase, stabilizers, red dye, surfactant and 0.1% sodium azide. The radial partition assay format described in Giegel et al. was used in all of the following experiments. Calibrator solutions A, B, C, D, E and F were prepared in a Tris-buffered solution (pH 7.5) including BSA, stabilizer and 0.1% sodium azide as a preservative. Calibrator solutions A, B, C, D, E and F contained concentrations of 0, 0.25. 0.75, 3, 12 and 50 uIU of hTSH per ml, respectively.

The assay is performed on the Stratus® II instrument by aspirating and delivering 60 ul of a selected calibrator (or sample) onto a tab. Twenty ul of the anti-hTSH alkaline phosphatase conjugate (0.75 ug/ml) are then delivered to each tab. The Stratus® instrument substrate probe then aspirates 70 ul of the substrate wash (pH 9.0 Tris buffer containing 1.0 mM 4-methylumbelliferyl phosphate, alkaline phosphatase inhibitor, stabilizers, blue dye, surfactant and 0.1% sodium azide) and releases 20 ul and 50 ul sequentially to the tab. As soon as the second substrate wash is delivered, the initial fluorescence rates are read and recorded in the instrument memory.

The amount of fluorescence generated by action of the phosphatase on the methylumbelliferyl phosphate substrate is detected by the Stratus® instrument and converted to a "rate" expressed in voltage per unit time, which is presented in the Tables and Figures as mV/min ("Stratus Rates"). The Stratus rate is a measure of the intensity of the fluorescence, which is, in turn, a measure of the amount of hTSH bound to the reactive portion of the tab.

During a Stratus® instrument run, the fluorescence rates of individual calibrators are measured and the values directed to storage locations in a microprocessor memory. After all calibrators have been measured, the program calculates "Rodbard" parameters A, B, C and D (Davis, S. E. et al., J. Immunoassay 1: 15–25 (1980)) using a multi-pass linear regression routine that fits a mathematical relationship to the measured data points in the form shown in the following equation:

$$R=\{(A-D)/[1+B(X/C)]+D\}$$

where R is the fluorescence rate and X is the corresponding concentration. The equation is a generalized sigmoidal curve that has been reported to give an excellent fit in various immunoassay systems. Based on the resulting A, B, C and D parameters stored in the memory, the instrument provides the concentration readout for the samples assayed.

Figure 3:
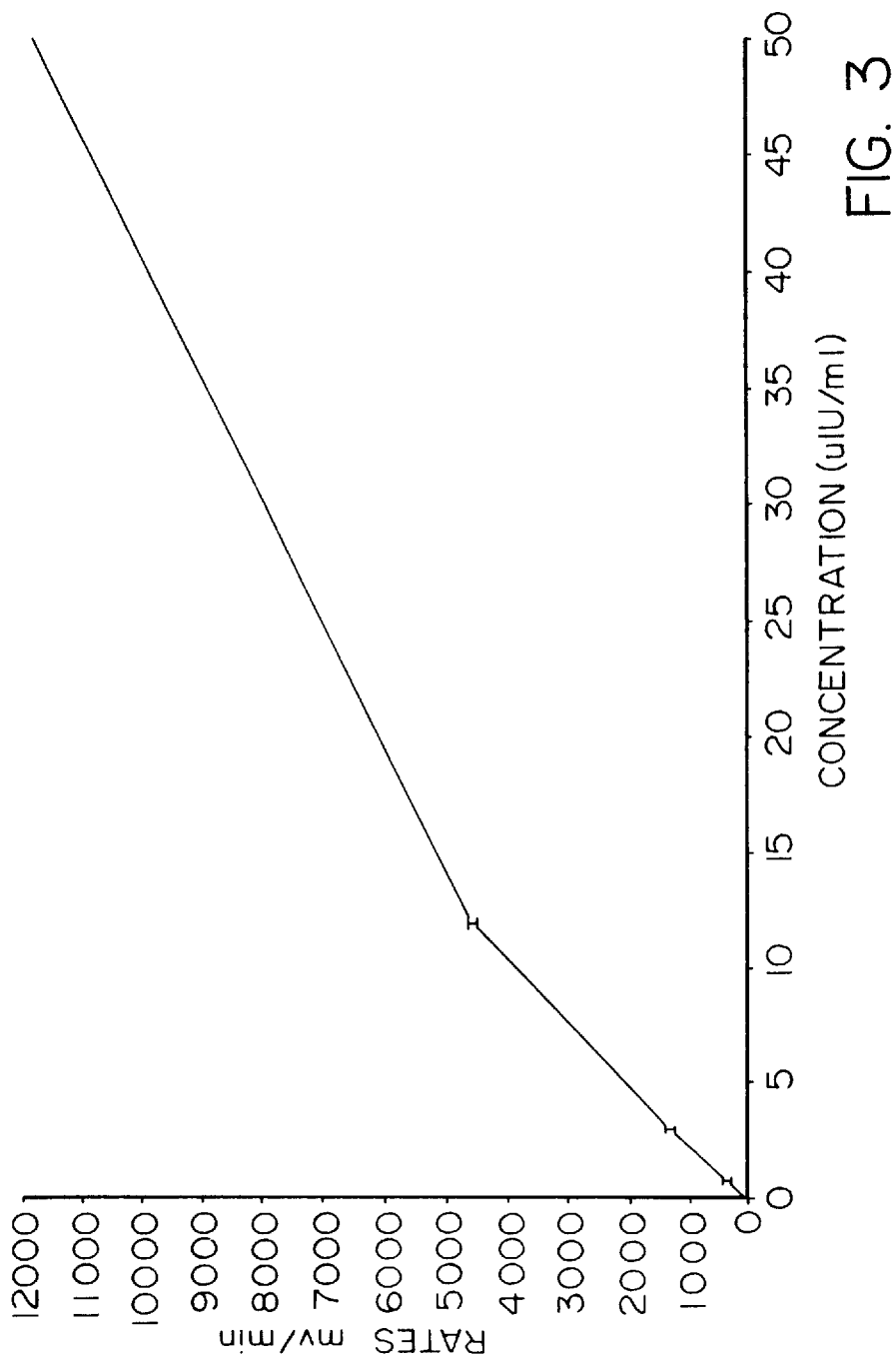
FIG. 3 depicts a calibration curve for various concentrations of hTSH using a direct specific binding assay format with monoclonal antibody CA2-dendrimer complexes.

Results of 5 replicate runs are presented in Table 1 and are depicted in graphical form in FIG. 3.

TABLE 1

CALIBRATION DATA FOR hTSH ASSAY USING IgG-DENDRIMER

| Calibrator | Average Rates | Standard Deviation | C.V. (%) |
|---|---|---|---|
| A | 43.5 | 10.07 | 23.2 |
| B | 142.4 | 5.97 | 4.19 |
| C | 392.18 | 9.82 | 2.51 |
| D | 1367.9 | 52.49 | 3.84 |
| E | 4580.6 | 99.26 | 2.17 |
| F | 11773.0 | 340.55 | 2.89 |

For these experiments, the CA2-DEND tabs were prepared in the Stratus® II instrument. That is, blank tabs were placed in the instrument and spotted with CA2-DEND solution using selected instrument parameters such that 76 ul CA2-DEND solution were applied to each tab at a flow rate of approximately 35 ul/sec from the sample probe.

Figure 4:
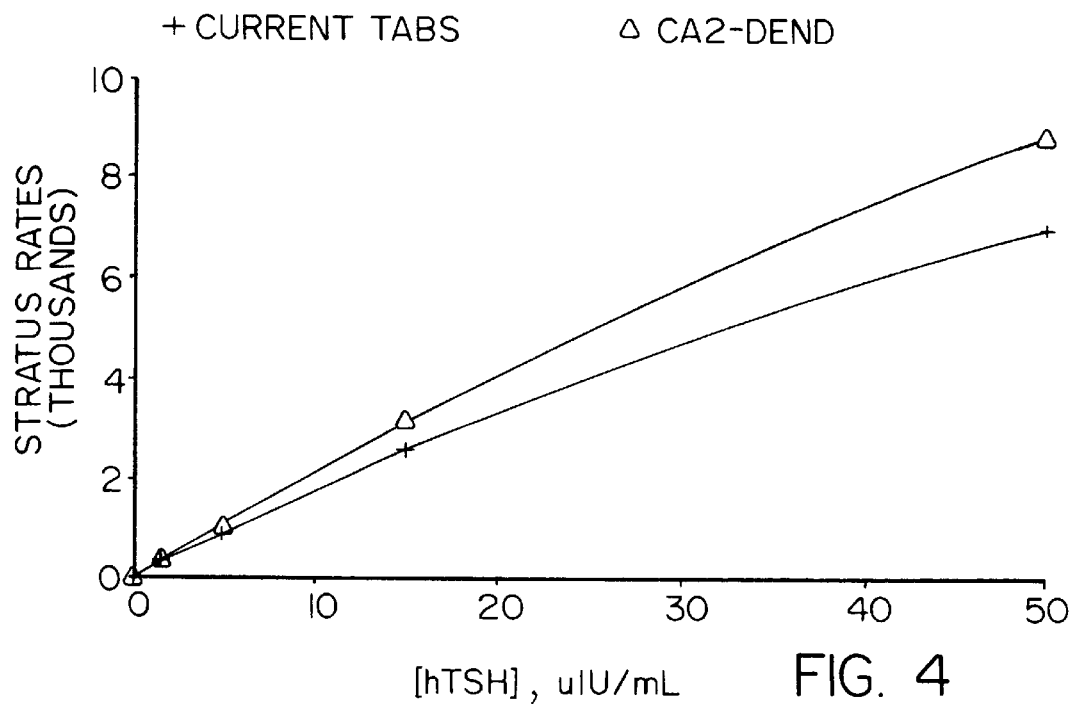
FIG. 4 depicts calibration curves for direct specific binding assays of hTSH with CA2-dendrimer complexes ("CA2-DEND") and with immunologically immobilized monoclonal antibody MAB-2-goat anti-IgG ("Current Tabs") complexes.
Figure 5:
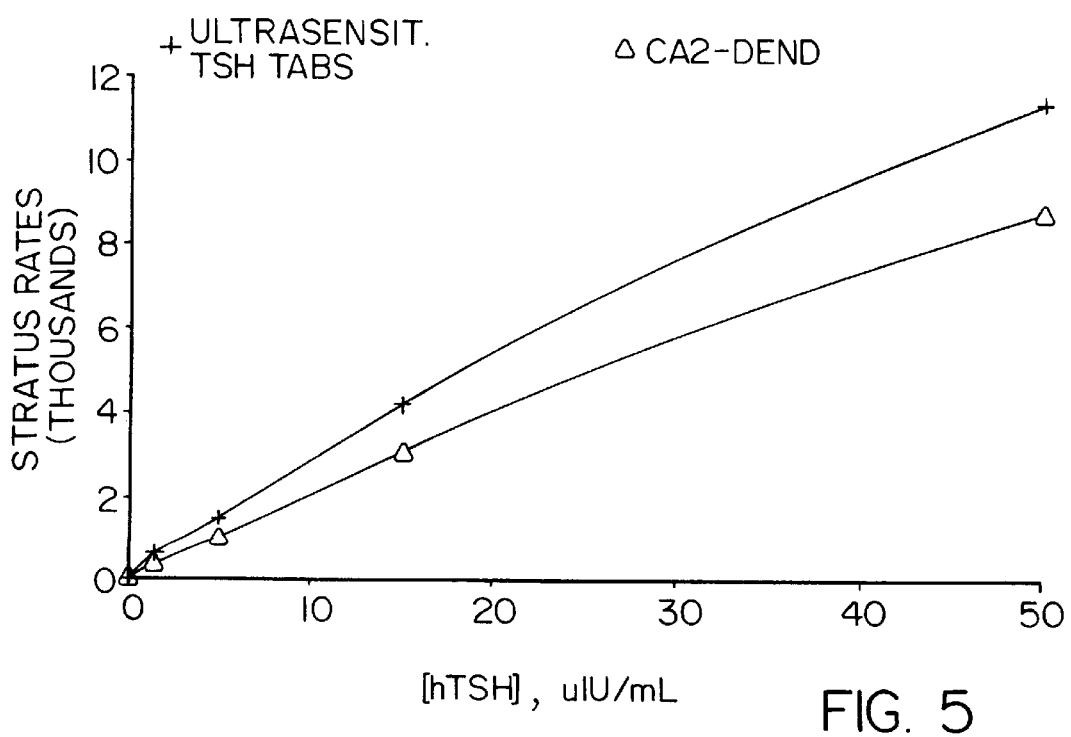
FIG. 5 depicts calibration curves for direct specific binding assays of hTSH with CA2-dendrimer complexes ("CA2-DEND) and with immunologically immobilized monoclonal antibody CA2-goat anti-IgG (""Ultrasensitive TSH Tabs") complexes.

In separate experiments, the performance of CA2-DEND tabs was compared with the performance of tabs presently marketed by Baxter Diagnostics Inc. and prepared using methods as generally described in U.S. Pat. No. 4,517,288 to Giegel et al (the "'288 patent"). That is, CA2-DEND or MAB-2 were immunologically immobilized on tabs as immunocomplexes. Both CA2 and MAB-2 are mouse anti-hTSH monoclonal antibodies, and each was complexed to secondary antibody comprising goat antiserum to mouse IgG. The resulting immunological complexes were adsorbed to blank tabs as described in the '288 patent. Tabs prepared in this manner were compared with CA2-DEND tabs in assays performed as described above. In these experiments, all tabs (including CA2-DEND) were prepared in an automated production system off-line of the Stratus® II instrument. In FIG. 4, tabs containing CA2-DEND at a concentration of 2.8 ug protein/tab are compared with immunologically immobilized tabs containing MAB-2-goat anti IgG at a concentration of 1.87 ug protein/tab. In FIG. 5, tabs containing CA2-DEND at a concentration of 11.3 ug protein/tab are compared with immunologically immobilized tabs containing CA2-goat anti-IgG at a concentration of 3.8 ug protein/tab.

Figure 6:
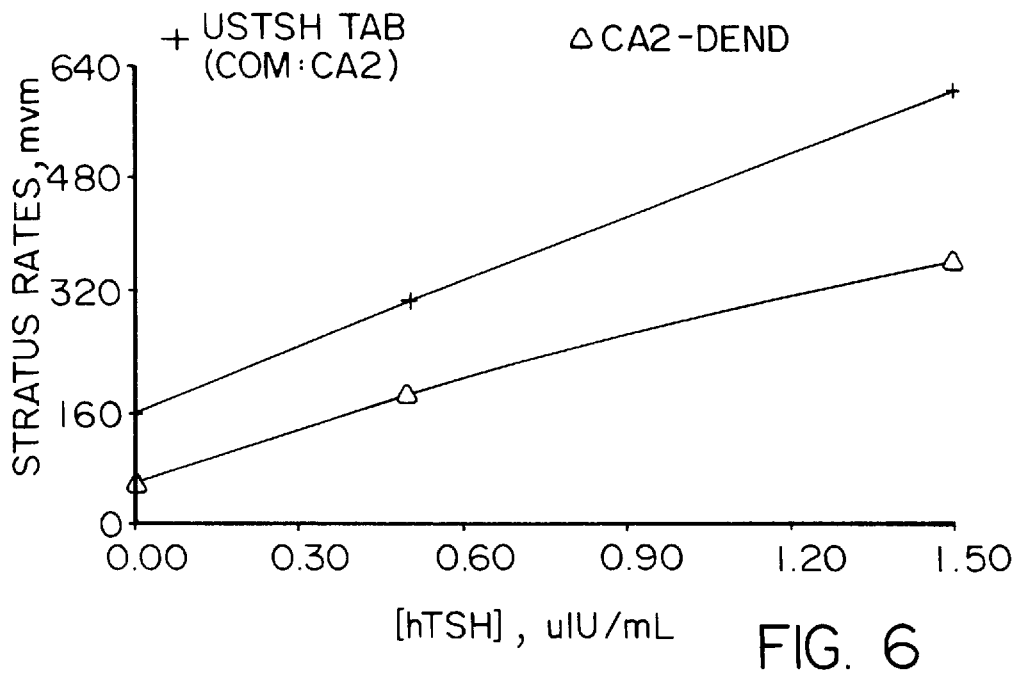
FIG. 6 depicts an expanded view of the lower end data depicted in FIG. 5.

The results demonstrate that CA2-DEND tabs are capable of generating calibration curves comparable to those obtainable with tabs prepared by immunological immobilization. FIG. 6 is an expanded version of the low end data shown in FIG. 5. The Y-axis intercept (calibrator A, zero units of hTSH) of 55 mV/min for the CA2-DEND tabs is significantly lower than the Y-axis intercept of 146 mV/min for the CA2 tabs prepared by immunological immobilization, reflecting a very low non-specific binding with dendrimer-based tabs. This permits more accurate reading of the low value calibrators with concomitant higher sensitivity at the low end of the assay calibration range.

EXAMPLE 5

Cortisol Assay

An immunoassay for cortisol was chosen to demonstrate application of the present invention to competitive immunoassay formats, to drug assays and to use of polyclonal antibodies.

Rabbit antiserum to cortisol (purchased from Ventrex, Mass., Cat. No. 4017100) was mixed 1:1 (v/v) with 100% saturated $(NH_4)_2SO_4$ at room temperature and the precipitate recovered by high-speed centrifugation at 2°–8° C. The pellet was dissolved in Bio-Rad protein A binding buffer (pH 9.0) (Cat. No. 153-6161) and applied to a Bio-Rad protein A-affi-gel column (Cat. No. 153-6154). The column was washed with the binding buffer until the UV absorbance of the flow-through dropped to baseline. Following this, the bound IgG was eluted with Bio-Rad elution buffer (pH 3.0) (Cat. No. 153-6162), then immediately buffer-exchanged into PBS/0.1% $NaN_3$.

The purified anti-cortisol polyclonal antibody was coupled to 54 Å dendrimers as described in EXAMPLE 1. The 54 Å dendrimer/anti-cortisol polyclonal antibody complexes (anti-cortisol DEND) in turn were spotted onto blank tabs in spotting buffer as described in EXAMPLE 3. Generally, the tabs were prepared by spotting 76 ul of 50 ug/ml of the anti-cortisol-DEND in spotting buffer (50 mM Tris, pH 8.0, 0.1% Zonyl® FSN, 2.0% BSA and 0.1% sodium azide) to blank tabs (i.e., 3.75 ug/tab) and dried. Calibrators A, B, C, D, E and F used in the competitive cortisol assays contained 0, 2.5, 5.0, 10.0, 25 and 50 ug cortisol per dl, respectively, made up in processed human serum containing 0.1% sodium azide as a preservative.

In the cortisol assay, the cortisol in a selected calibrator competes with a labeled cortisol analogue for binding with the anti-cortisol DEND immobilized on the tab. The assay is performed by mixing 20 ul of calibrators (or sample) in sample cups with 40 ul of analogue solution ( 0.5 ug/ml cortisol-calf intestinal alkaline phosphatase conjugate in pH 8.0 Tris buffer, stabilizers, red dye, surfactant and 0.1% $NaN_3$) and 220 ul of cortisol assay buffer (30 mM sodium phosphate, 8-anilino-1-naphthalenesulfonic acid and 0.1% sodium azide, pH 5.5) using a Stratus® Automated Sample Handler (SASH). The tray containing the cups is then transferred to a Stratus® instrument. Seventy ul of solution in each cup are aspirated and delivered to a tab containing anti-cortisol-DEND. The Stratus® instrument substrate probe then aspirates 70 ul of the substrate wash (pH 9.0 Tris buffer containing 1.0 mM 4-methylumbelliferyl phosphate, alkaline phosphatase inhibitor, stabilizers, blue dye, surfactant and 0.1% sodium azide) and releases 20 ul and 50 ul sequentially to the tab. As soon as the second substrate wash is delivered, the initial fluorescence rates are read and recorded in the instrument memory. After the calibration curve is formed and Rodbard's parameters are generated, a concentration for each sample is printed out.

Figure 7:
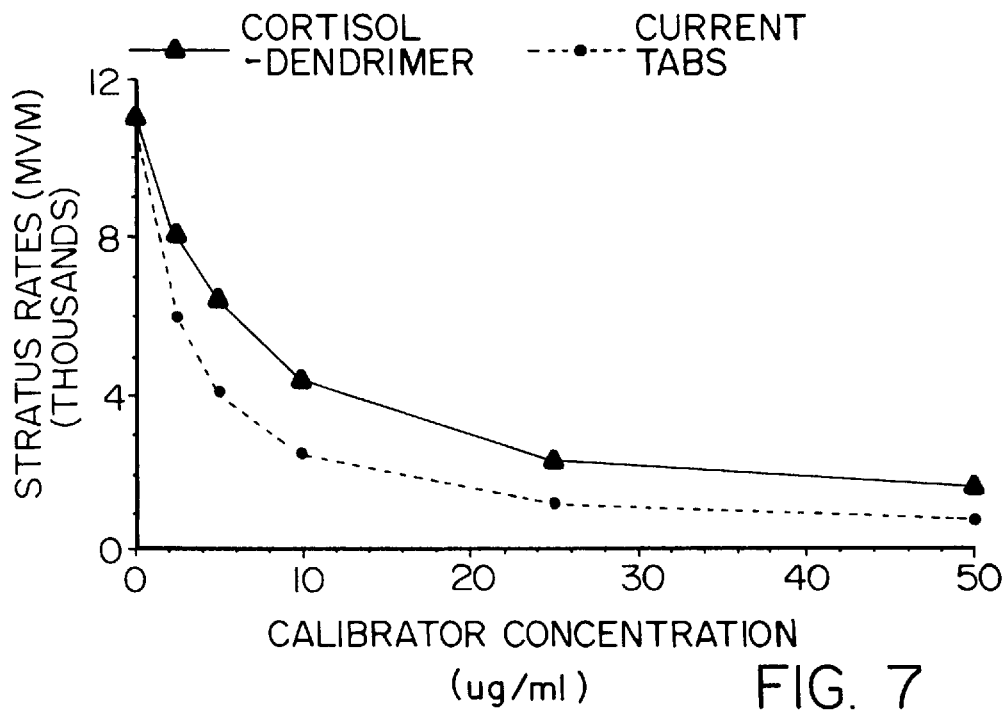
FIG. 7 depicts calibration curves for competitive immunoassays of cortisol with anti-cortisol polyclonal antibody-dendrimer complexes ("Cortisol-Dendrimer") and with immunologically immobilized anti-cortisol antibody ("Current Tabs").

In FIG. 7, results of competitive assay runs with anti-cortisol-DEND tabs are compared to results of similar assays run with anti-cortisol tabs prepared by immunological immobilization. The tabs prepared by immunological immobilization ("current tabs" in FIG. 7) were manufactured by spotting blank tabs with a solution containing rabbit anti-cortisol serum complexed with goat antiserum to rabbit IgG, surfactant, stabilizer, blue/green dye and 0.1% sodium azide. In FIG. 7, tabs containing anti-cortisol-DEND at a concentration of 3.75 ug protein/tab are compared with immunologically immobilized tabs containing anti-cortisol polyclonal antibody at a concentration of 858 ng protein/tab. The shapes of the calibration curves are comparable for the two types of tabs.

EXAMPLE 6

Folate Assay

The following assay demonstrates the utility of dendrimers coupled to molecules other than polypeptides, i.e., dendrimers coupled to small molecules such as folic acid.

For production of dendrimer coupled to folic acid (folate-DEND), 1.5 ml of 54 Å dendrimer as supplied by the vendor (approximately $4.0 \times 10^{16}$ particles/ml) are added to 0.3 ml of 0.5M sodium phosphate (pH 7.1). The pH of the solution is adjusted to approximately 7.6 with 1N HCl or 1N NaOH. Then, 1.2 mg of N-hydroxysuccinimide-activated folic acid is dissolved in 0.12 ml of dimethylsulfoxide and added to the pH 7.6 dendrimer solution. The combined solutions represent a molar ratio of 20:1 activated folic acid:dendrimer. The reaction mixture is incubated at room temperature for 2 hrs. The reaction is quenched by adding 0.14 ml of 1 M ethanolamine hydrochloride. The reaction mixture is incubated an additional ½ hr at room temperature, then desalted by passage over a Sephadex G-25 column equilibrated with PBS/0.1% $NaN_3$, pH 7.4. The molar concentration of folate is estimated using a molar extinction coefficient at 350 nm of 7,400 $cm^{-1} M^{-1}$.

For production of enzyme-labelled folate binding protein (FBP-ALP), calf intestinal alkaline phosphatase (ALP) is prepared in 0.1M sodium phosphate, 1 mM Mg++, pH 7.6. The volume of the ALP solution is adjusted to a final concentration of 2.6 mg ALP/ml. The ALP solution is combined with a 2 mg/ml solution of sulfo-SIAB at a molar ratio of 20:1 sulfo-SIAB:ALP. The reaction mixture is incubated for 1 hr at 30° C., then desalted by passage over a Sephadex G-25 column equilibrated with 0.1M sodium phosphate, 1 mM Mg++, pH 7.6. The protein fractions are pooled and the concentration of SIAB-labeled ALP (ALP-SIAB) is determined with a BCA protein assay (Pierce, Cat. No. 23225G). The number of SIAB groups per ALP molecule may be determined with standard methods known to those skilled in the art.

To 5 mg of FBP in 2.13 ml of 0.12M sodium phosphate (pH 7.5) is added 85 ul of dimethylformamide containing 174 mg of S-acetylmercaptosuccinic anhydride. The solution is incubated for 1 hr at 30° C., followed by addition of 22 ul of 1M hydroxylamine in 0.1M sodium phosphate (pH 7.6) and an additional ½-hr incubation at 30° C. The solution is then desalted by passage over a Sephadex G-25 column equilibrated with 0.1M sodium phosphate, 5 mm EDTA (pH 6.0). The protein fractions are pooled and the FBP sulfhydryl derivative (FBP-SH) concentration is determined using an extinction coefficient at 280 nm of approximately 3.57 $ml \cdot mg^{-1} \cdot cm^{-1}$. The number of sulfhydryl groups per FBP molecule may be determined with standard procedures known to those skilled in the art.

The ALP-SIAB (MW 140,000 daltons) and FBP-SH (MW 30,000 daltons) solutions are combined at molar ratios of 1:6, respectively, and the combined solution volume adjusted so that the total protein concentration is 4–5 mg/ml. The combined solution is buffer-exchanged into 0.1M sodium phosphate, 1 mM Mg++ (pH 7.6), then incubated at 2°–8° C. for 24 hrs. The reaction is quenched by addition of 10 mg/ml of N-ethylmaleimide in dimethylformaldehyde equal to ⅟₅₀ of the reaction volume, and an additional incubation at room temperature for 2 hrs. The resulting conjugate is purified by passage over an AcA-34 Ultrogel column equilibrated with 10 mM Tris, 1 mM Mg++, 0.1 mM Zn++, and 0.1% sodium azide (pH 7.0). Concentration of the FBP-ALP conjugate in the pooled fractions may be determined with the Pierce BCA protein assay.

The folate assay was carried out in the competitive format using the Stratus® instrument and conditions similar to those reported above for the cortisol competitive assay. In the folate assay, the folic acid in a selected calibrator (or sample) competes with the folate moiety on the folate-DEND particles for binding to the FBP-ALP conjugate. That is, progressively higher folate concentrations in the calibrator or sample will cause correspondingly lower levels of FBP-ALP to be bound to the folate-DEND on the solid phase (tab). Folate in serum exists in association with folate binding protein which interferes with measurements of folate based on specific binding of assay reagents. Other serum proteins also can interfere through specific or non-specific interactions with folate and other assay reagents. As such, the folate to be measured needs to be liberated from folate binding protein and from interfering association with other serum proteins. To this end, a folate extractant containing 1N NaOH in 25% ethanol, and a folate reductant containing dithiothreitol (DTT), ethylenediaminetetraacetic acid (EDTA), NaCl and sodium phosphate (pH 6.3) are included in the assays. A folate neutralizer containing borate (pH 7.2) and 0.5% folate-free BSA is added to neutralize the folate extractant and reductant at the appropriate time in the assay.

Figure 8:
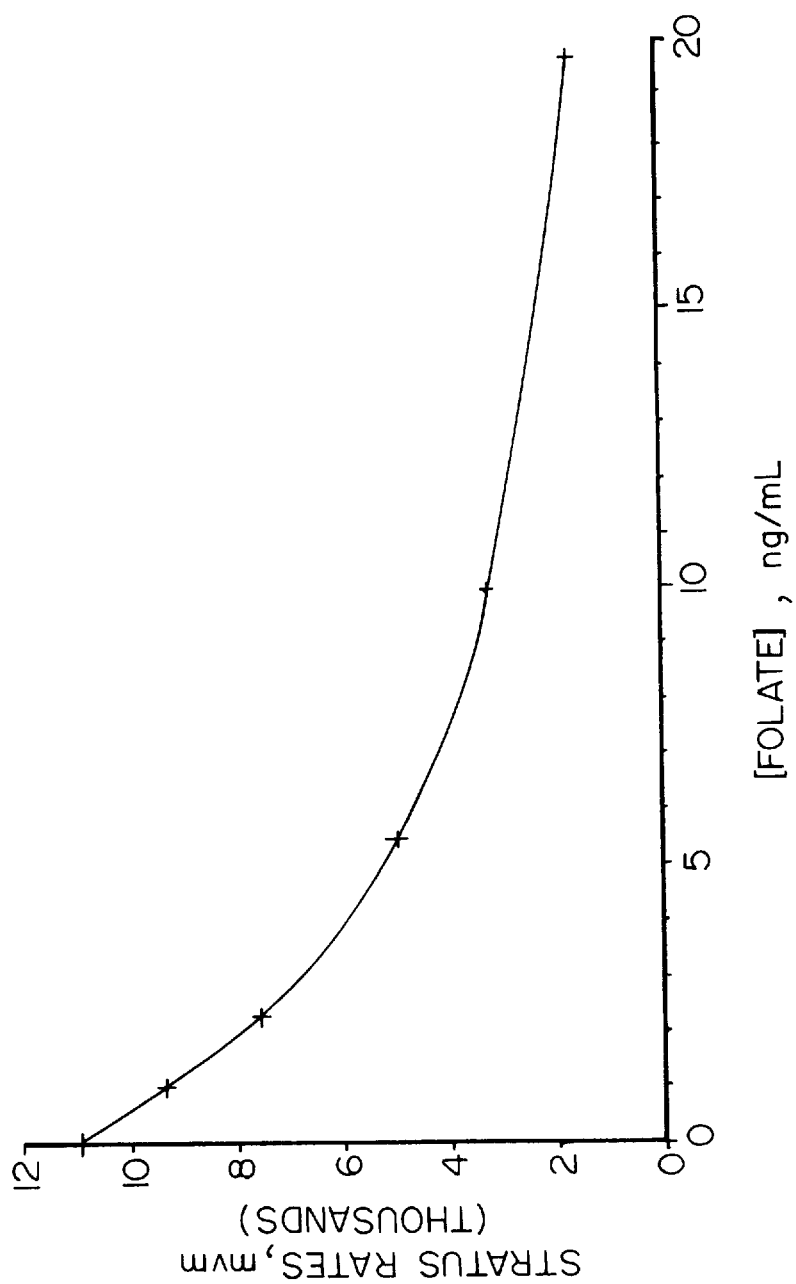
FIG. 8 depicts a calibration curve for various concentrations of folate using a competitive assay format with folate-dendrimer complexes.

Each assay tab was made up by spotting 76 ul of 6.5 ug/ml folate-DEND in spotting buffer with 5% folate-free BSA onto the central area of the tab, as described in EXAMPLE 3, above. Calibrators A, B, C, D, E and F used in the competitive folate assays contained 0, 0.90, 2.20, 5.40, 9.90 and 19.60 ng folate/ml in processed human serum, respectively. The assay is performed by mixing 70 ul of a selected calibrator in a sample cup with 20 ul folate reductant, followed by addition of 20 ul folate extractant, followed by addition of 160 ul of 0.625 ug/ml FBP-ALP in folate neutralizer. After a 20 minute incubation, the mixture is spotted onto a folate-DEND tab, washed with substrate wash as described above in the cortisol assay (EXAMPLE 5), and the fluorescence rates taken and recorded. Results of these experiments are given in FIG. 8.

The foregoing detailed description has been provided for a better understanding of the invention only and no unnecessary limitation should be understood therefrom as some modifications will be apparent to those skilled in the art without deviating from the spirit and scope of the appended claims.

What is claimed is:

1. A specific binding assay complex comprising:
    (a) a solid phase; and
    (b) a dendrimer-reagent complex comprising a dendrimer having an outer functionalized surface and a specific binding assay reagent covalently coupled to said outer functionalized surface, said dendrimer-reagent complex immobilized on said solid phase, said specific binding assay complex having interstices.

2. The specific binding assay complex of claim 1, wherein said solid phase is a glass fiber filter comprising a plurality of enmeshed glass fibers.

3. The specific binding assay complex of claim 2, wherein said glass fiber filter has a substantially negatively charged surface and said dendrimer has a substantially positively charged surface.

4. The specific binding assay complex of claim 1, wherein said dendrimer comprises an initiator core, at least one inner layer, and an outer functionalized surface.

5. The specific binding assay complex of claim 1, wherein said dendrimer is a 54 Å dendrimer and said outer functionalized surface comprises a plurality of amine groups.

6. The specific binding assay complex of claim 1, wherein said specific binding assay reagent is a polypeptide.

7. The specific binding assay complex of claim 6, wherein said polypeptide is selected from the group consisting of an antibody, an antibody fragment, and a specific binding protein.

8. The specific binding assay complex of claim 6, wherein said polypeptide is selected from the group consisting of an anti-hTSH antibody, an anti-cortisol antibody and folate binding protein.

9. The specific binding assay complex of claim 1, wherein said specific binding assay reagent is an analyte.

10. The specific binding assay complex of claim 9, wherein said analyte is folate.

11. A method for immobilizing a specific binding assay reagent on a solid phase, comprising:
    (a) covalently coupling said reagent to a dendrimer; and
    (b) contacting said dendrimer with said solid phase under conditions effecting immobilization of said dendrimer on said solid phase.

12. The method of claim 11 wherein said reagent is selected from the group consisting of an antibody, an antibody fragment, a specific binding protein and an analyte.

13. The method of claim 11 wherein said covalent coupling of said reagent to said dendrimer is by C—N linkage carried out by Schiff base reduction.

14. The method of claim 11 wherein said covalent coupling of said reagent to said dendrimer is by C—S linkage carried out by combining SIAB-labeled moieties with sulfhydryl-containing moieties.

15. The method of claim 11 wherein said covalent coupling of said reagent to said dendrimer is by C—O linkage carried out by reaction of cyanogen bromide-activated dendrimer with amino groups of said reagent.

16. A method for conducting a specific binding assay to determine the concentration or presence of an analyte or receptor of said analyte in a sample, comprising:
    (a) applying said sample to a solid phase, said solid phase having effective amounts of an immobilized dendrimer-reagent complex, said complex formed by covalently coupling a specific binding assay reagent with specificity for said analyte or for a receptor of said analyte to a dendrimer, said sample applied under conditions effecting binding of said analyte or receptor of said analyte to said reagent;
    (b) applying a selected amount of labeled conjugate to said solid phase under conditions effecting binding of said conjugate to said analyte or receptor of said analyte;
    (c) determining the amount of said labeled conjugate bound to said analyte or receptor of said analyte on said solid phase; and
    (d) correlating said amount of said labeled conjugate with the concentration or presence of said analyte or receptor of said analyte in said sample.

17. The method of claim 16 wherein said reagent is selected from the group consisting of an antibody, an antibody fragment, a specific binding protein and an analyte.

18. The method of claim 16 wherein said sample and said labeled conjugate are applied simultaneously to said solid phase.

19. A method for conducting a specific binding assay to determine the concentration or presence of an analyte or receptor of said analyte in a sample, comprising:
    (a) applying said sample to a solid phase, said solid phase having effective amounts of an immobilized dendrimer-reagent complex, said complex formed by covalently coupling a specific binding assay reagent with specificity for said analyte or for a receptor of said analyte to a dendrimer, said sample applied under conditions effecting binding of said analyte or receptor of said analyte to said reagent;
    (b) applying a selected amount of labeled specific competitive reagent to said solid phase under conditions effecting binding of said competitive reagent to said complex;

(c) determining the amount of label bound to said complex on said solid phase; and (d) correlating said amount of said label with the concentration or presence of said analyte or receptor of said analyte in said sample.

20. The method of claim 19 wherein said specific competitive reagent is a labeled analogue of said analyte.

21. The method of claim 19 wherein said specific competitive reagent is a labeled receptor for said analyte.

22. The method of claim 19 wherein said reagent is selected from the group consisting of an antibody, an antibody fragment, a specific binding protein and an analyte.

23. The method of claim 11 wherein said covalent coupling of said reagent to said dendrimer is performed prior to contacting said dendrimer with said solid phase.

24. A method for immobilizing a specific binding assay reagent, comprising:

(a) covalently coupling said reagent to a dendrimer; and (b) contacting said dendrimer with a solid phase having interstices therein under conditions effecting immobilization of said dendrimer on said solid phase, thereby forming a specific binding assay complex having interstices.

25. The method of claim 24 wherein said covalent coupling of said reagent to said dendrimer is performed prior to contacting said dendrimer with said solid phase.

26. The method of claim 24 wherein said reagent is selected from the group consisting of an antibody, an antibody fragment, a specific binding protein and an analyte.

27. The method of claim 24 wherein said covalent coupling of said reagent to said dendrimer is by C—N linkage carried out by Schiff base reduction.

28. The method of claim 24 wherein said covalent coupling of said reagent to said dendrimer is by C—S linkage carried out by combining SIAB-labeled moieties with sulfhydryl-containing moieties.

29. The method of claim 24 wherein said covalent coupling of said reagent to said dendrimer is by C—O linkage carried out by reaction of cyanogen bromide-activated dendrimer with amino groups of said reagent.

30. A method for conducting a specific binding assay to determine the concentration or presence of an analyte or receptor of said analyte in a sample, comprising:

(a) applying said sample to a specific binding assay complex having interstices, said specific binding assay complex comprising a solid phase and effective amounts of an immobilized dendrimer-reagent complex, said dendrimer-reagent complex formed by covalently coupling a specific binding assay reagent with specificity for said analyte or for a receptor of said analyte to a dendrimer, said sample applied under conditions effecting binding of said analyte or receptor of said analyte to said reagent;

(b) applying a selected amount of labeled conjugate to said solid phase under conditions effecting binding of said conjugate to said analyte or receptor of said analyte;

(c) determining the amount of said labeled conjugate bound to said analyte or receptor of said analyte on said solid phase; and (d) correlating said amount of said labeled conjugate with the concentration or presence of said analyte or receptor of said analyte in said sample.

31. The method of claim 30 wherein said reagent is selected from the group consisting of an antibody, an antibody fragment, a specific binding protein and an analyte.

32. The method of claim 30 wherein said sample and said labeled conjugate are applied simultaneously to said solid phase.

33. A method for conducting a specific binding assay to determine the concentration or presence of an analyte or receptor of said analyte in a sample, comprising:

(a) applying said sample to a specific binding assay complex having interstices, said specific binding assay complex comprising a solid phase and effective amounts of an immobilized dendrimer-reagent complex, said dendrimer-reagent complex formed by covalently coupling a specific binding assay reagent with specificity for said analyte or for a receptor of said analyte to a dendrimer, said sample applied under conditions effecting binding of said analyte or receptor of said analyte to said reagent;

(b) applying a selected amount of labeled specific competitive reagent to said solid phase under conditions effecting binding of said competitive reagent to said complex;

(c) determining the amount of label bound to said complex on said solid phase; and (d) correlating said amount of said label with the concentration or presence of said analyte or receptor of said analyte in said sample.

34. The method of claim 33 wherein said specific competitive reagent is a labeled analogue of said analyte.

35. The method of claim 33 wherein said specific competitive reagent is a labeled receptor for said analyte.

36. The method of claim 33 wherein said reagent is selected from the group consisting of an antibody, an antibody fragment, a specific binding protein and an analyte.

* * * * *